United States Patent [19]

Lobdell et al.

[11] 4,432,767
[45] Feb. 21, 1984

[54] TUBING INJECTION SITE GUARD

[75] Inventors: Donn D. Lobdell, Golden; Thomas E. Goyne, Denver, both of Colo.

[73] Assignee: Cobe Laboratories, Inc., Lakewood, Colo.

[21] Appl. No.: 852,058

[22] Filed: Nov. 16, 1977

[51] Int. Cl.³ .......................... A61M 5/00; A61M 5/03
[52] U.S. Cl. .................................................. 604/86
[58] Field of Search .......... 128/214 R, 214 Z, 214 H, 128/214.2, 2 F, 247, 334 C; 137/318; 285/419, 373, 197; 138/137; 24/255 SL; 203/234; 604/86, 201

[56] References Cited

U.S. PATENT DOCUMENTS

| | | | |
|---|---|---|---|
| 3,447,570 | 6/1969 | Collins | 128/214 X |
| 3,456,965 | 7/1969 | Gasewski et al. | 128/334 C X |
| 3,682,163 | 8/1972 | Plummer | 24/255 SL |
| 3,711,632 | 1/1973 | Ghirardi | 285/419 X |
| 3,850,202 | 11/1974 | Morgan | 128/214 R X |
| 3,898,988 | 8/1975 | Morgan | 128/214 R |
| 3,913,187 | 10/1975 | Okuda | 24/255 SL |
| 4,043,333 | 8/1977 | Munsch | 128/214 R |
| 4,076,023 | 2/1978 | Martinez | 128/214 R |
| 4,112,449 | 9/1978 | Williams | 128/214 R |

*Primary Examiner*—James R. Feyrer

[57] ABSTRACT

A tubing injection site guard comprising a compressible, penetrable sleeve for surrounding a continuous tube and a rigid casing enclosing the sleeve. The casing comprises two opposing longitudinal sections longitudinally hinged, with a needle access port in one section to allow insertion of a needle through the sleeve and into the tube. The sections are capable of being locked together to radially compress the sleeve over its entire length and thereby seal needle holes. An adjustable locking means is provided to lock the sections together and to allow adjustment of the radial compression. The site guard also protects the operator from injury while inserting the needle by enclosing the entire injection site except at the needle access port.

8 Claims, 2 Drawing Figures

4,432,767

TUBING INJECTION SITE GUARD

FIELD OF THE INVENTION

This invention relates to a tubing injection site guard for permitting a needle to be inserted into a tube containing blood or other fluid and withdrawn without subsequent leakage from the tube.

BACKGROUND OF THE INVENTION

There is a common medical requirement for directly introducing drugs into the bloodstream of a patient, or taking blood samples, at an extracorporeal point, e.g., one of the blood conducting tubes between the patient and an artificial kidney. Access to the blood in the tubing is accomplished by inserting a hypodermic needle into the tubing, but insertion of the needle results in problems in resealing the tubing after the needle is withdrawn and in protecting the operator from accidents while inserting the needle.

Morgan U.S. Pat. No. 3,850,202 describes a tubing injection site guard in which an elastomeric tube is placed in the blood line between the ends of two pieces of blood tubing and all three tubes are surrounded by a rigid sleeve having a needle access port. The elastomeric tube is compressed by the sleeve so that the needle hole reseals. This design requires that the blood tubing be cut and adhesively bonded joints formed between the two sections of blood tubing and the sleeve. It would be desirable not to have to cut the blood tubing and not to have to rely on adhesively bonded joints that could fail in use. Also, the compression of the rubber tube cannot be adjusted with use should the built-in compression not provide adequate sealing after a period of time and use.

Morgan U.S. Pat No. 3,898,988 describes a tubing injection site guard comprising a rigid plastic tube connecting the ends of two pieces of blood tubing; the needle access port is an opening in the wall of the rigid tube which is sealed with a plug of polyurethane or similar material placed under compression by the sides of the opening. This design also requires adhesively bonded joints between the blood tubing and the rigid tube, and does not allow adjustment of the compression on the sealing plug.

Collins U.S. Pat. No. 3,447,570 describes a tubing injection site guard comprising a U-shaped rigid base engaging a latex pad to form a cylindrical space through which the blood tubing passes. While avoiding tubing joints, the latex is not directly compressed against the blood tubing and needle hole, and the compression cannot be adjusted with use should the built-in compression not be sufficient for sealing after a period of use.

SUMMARY OF THE INVENTION

We have discovered that the problems of leakage, tubing joints, and deterioration of sealing with time and use can be solved by the invention described herein, which provides a jointless tubing injection site guard with adjustable radial compression of the hole sealing means. The injection site guard comprises a compressible, penetrable sleeve surrounding the blood tube and a longitudinally divided and hinged rigid casing enclosing the sleeve. The opposing casing sections are brought together to radially compress the sleeve against the tubing over the entire length of the sleeve, thereby sealing the sleeve against the tube and sealing the needle holes. One section of the casing has a needle access port. A means for locking the casing sections together is provided which allows the compression of the sleeve to be adjusted during use. The casing surrounds the needle injection site except for the needle access port, thereby protecting the operator from injury while inserting the needle.

In preferred embodiments the casing is generally cylindrical and the casing sections are generally semicylindrical. The locking means includes a pair of ears, one ear extending from each casing section, and one ear having two spaced apart ratchets and the other ear having two correspondingly spaced apart pawls. The hinge comprises a longitudinal casing portion of reduced thickness. Casing extensions on both ends of the casing enclose and support the blood tubing to prevent bending stresses imposed on the blood tube from being communicated to the length of tube within the sleeve, thereby preventing distortion of the tube and sleeve in this length and leaks arising from such distortion. In addition, the inside diameter of the casing is reduced in the area about the needle access port to allow for tolerances in the diameters of the sleeve and tubing, e.g., when they are of smaller than normal diameter. Finally, the casing is a single piece of plastic incorporating the casing sections, hinge, locking means, and cylindrical extensions.

In addition to preventing leaks from the blood tubing and protecting the operator during insertion of the needle, the invention described herein is safe in use in that there are no tubing joints that could fail under operating conditions and in that it does not require nor allow incompatible materials to come into contact with the blood. The invention is easy to use, inexpensive, and easy to manufacture.

DESCRIPTION OF THE PREFERRED EMBODIMENT

The structure and operation of the preferred embodiment of the invention follow:

Structure

The drawings show the preferred embodiment, which is then described.

1. Drawings

2. Description

Figure 1:
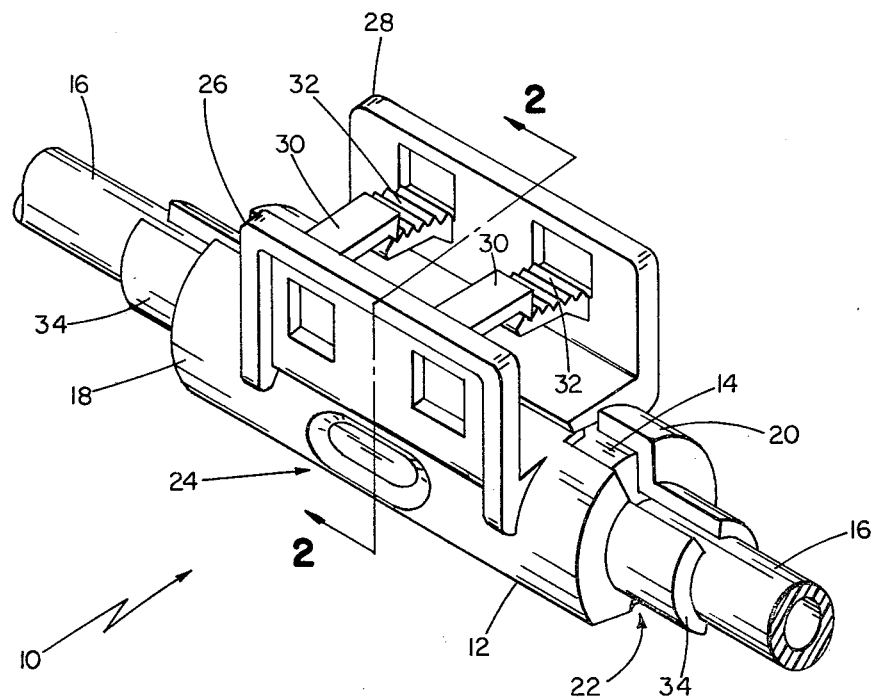
FIG. 1 is an isometric view of the presently preferred embodiment of the invention as installed on a tube.

As shown in FIG. 1, tubing injection site guard 10 has rigid casing 12 enclosing compressible, penetrable sleeve 14, which in turn surrounds blood tube 16. Casing 12 is made of plastic, and sleeve 14 is made of latex, while tube 16 is commonly vinyl.

Casing 12 is longitudinally divided into opposing casing sections 18 and 20, which are joined by hinge 22. Casing 12 is generally cylindrical and casing sections 18 and 20 generally semicylindrical in shape, but the casing and its sections deviate from this form in the area of hinge 22 and in the portions of casing sections 18 and 20 diametrically opposite to hinge 22 to allow for the operation of hinge 22 and to allow casing sections 18 and 20 to be brought closer together about sleeve 14.

Casing section 18 has needle access port 24 midway along its length, while casing section 20 is continuous throughout its length. Needle access port 24 allows a needle to be inserted through port 24 and sleeve 14 into tube 16. Casing 12 radially compresses sleeve 14 over its entire length, preventing leaks from tube 16 after the needle is withdrawn by sealing sleeve 14 against tube 16 and compressing closed the needle hole in sleeve 14. Casing 12 also protects the operator from injury while inserting the needle by enclosing the needle injection site except at needle access port 24.

Casing sections 18 and 20 have ears 26 and 28, with ear 26 having two spaced-apart pawls 30 and ear 28 having two correspondingly spaced-apart ratchets 32. Ears 26 and 28 are for finger manipulation by the operator, allowing the operator to apply compressive force to sleeve 14 by closing casing sections 18 and 20 about sleeve 14. Pawls 30 and ratchets 32 lock casing sections 18 and 20 in the closed position about sleeve 14, maintaining the radial compression on sleeve 14 and allowing further compression to be applied as required.

Casing extensions 34 extend from each longitudinal end of casing sections 18 and 20 and have an inner diameter slightly greater than the outer diameter of tube 16. Extensions 34 enclose and support tube 16 at both ends of casing 12 to prevent bending stresses imposed on tube 16 from being communicated to the section of tube 16 enclosed by casing 12 and sleeve 14, thereby preventing distortion of tube 16 and sleeve 14 in this area and leaks arising from such distortion.

Figure 2:
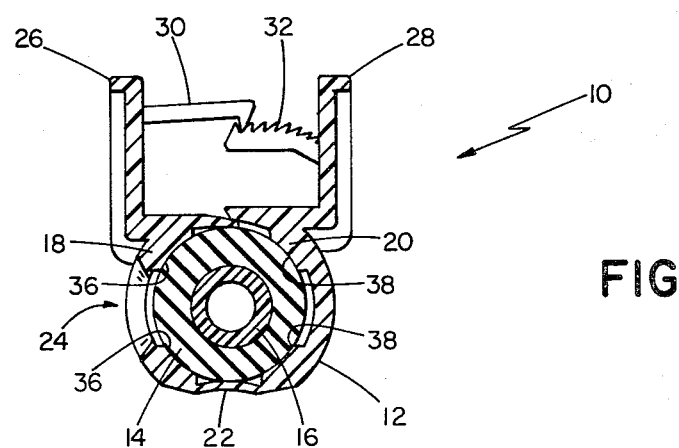
FIG. 2 is a sectional view through 2—2 of FIG. 1.

As shown in FIG. 2, the inner diameter of casing 12 is reduced in the area surrounding needle access port 24 by raised areas 36 and 38 on casing sections 18 and 20. Raised areas 36 and 38 are trapezoidal in shape, extending symmetrically and longitudinally on both sides of port 24 and have a total average longitudinal dimension equal to approximately twice the longitudinal dimension of port 24. The sides of raised areas 36 and 38 adjacent to hinge 22 are of approximately equal length, and areas 36 and 38 together describe a trapezoid with its longer side adjacent to ear 26 and its shorter side adjacent to ear 28. The reduction in the inner diameter of casing 12 in the area of port 24 allows for tolerances in the diameters of sleeve 14 and tube 16. Raised areas 36 and 38 provide greater compression in the area around port 24, where the needle is inserted and thus where such compression is most needed. The raised areas thus compensate for sleeve 14 or tube 16's being smaller in diameter than normal. The greater inner diameter of casing 12 outside of areas 36 and 38 reduces the compressive force on sleeve 14 outside those areas to reduce the force forcing open casing 12 when sleeve 14 or tube 16 is of greater than normal diameter. The trapezoidal shape of raised areas 36 and 38 provides improved flow of the plastic from which casing 12 is made when casing 12 is manufactured as an injection molded piece as described below; the trapezoidal shape feature is the contribution of William Reickmann. A section of raised area 38 diametrically opposite to port 24 and generally of similar shape and dimensions as port 24 is recessed, allowing for the insertion of a manufacturer's part number during the molding process.

Tubing injection site guard 10 is assembled for use by first placing sleeve 14 over tube 16. Sleeve 14 is placed over tube 16 at one end of tube 16 and moved along tube 16 to the desired location for guard 10. This step is implemented by either lubricating sleeve 14 and tube 16 or by mechanically expanding sleeve 14. Casing 12, initially laid open as molded, is then placed around sleeve 14 and ears 26 and 28 forced together to close casing sections 18 and 20 around hinge 22 to enclose sleeve 14 until pawls 30 and ratchets 32 first engage (FIG. 1) to hold casing sections 18 and 20 together.

Regarding dimensions, blood tube 16 has an outer diameter of approximately ¼ inch and the outer diameter of sleeve 14 is approximately ½ inch. Casing 12 is 1 11/16 inches in length with casing extensions 34 having a length of ¼ inch. Ears 26 and 28 extend approximately ½ inch from casing 12, and needle access port 24 is approximately 5/16 inch longitudinally by ⅛ inch wide. Raised areas 36 and 38 are 10 mils in thickness.

In the preferred embodiment, casing 12 is injection molded as a single integral piece, incorporating casing sections 18 and 20, ears 26 and 28, pawls 30, ratchets 32, and extensions 34, from unfilled 6/6 nylon, with hinge 22 formed by longitudinally reducing the thickness of casing 12 between casing sections 18 and 20.

Operation

Just before an injection is made, ears 26 and 28 are squeezed together to compress sleeve 14 further. Pawls 30 and ratchets 32 will maintain the compression of sleeve 14 when ears 26 and 28 are released. A needle is then inserted through needle access port 24 and sleeve 14 into tube 16. The operation of ratchets 32 and pawls 30 allows the compression of sleeve 14 to be subsequently increased if necessary, e.g., for subsequent injections or to compensate for a reduction in the diameter of tube 16 due to cold flow of the vinyl comprising tube 16.

What is claimed is:

1. A tubing injection site guard comprising:
    a compressible, penetrable sleeve adapted to surround a continuous tube,
    a longitudinally divided rigid casing comprising
        two casing sections,
            one of said casing sections having a needle access port,
            said casing sections having walls, said wall of one said casing section being spaced-apart from the other said wall,
        a longitudinal hinge joining said casing sections along one longitudinal side, and
        means for locking said casing sections together around said sleeve in an adjustable relationship therebetween,
            said needle access port allowing a needle to be inserted through said needle port and said sleeve into said tubing,
            said casing radially compressing said sleeve throughout the length of said sleeve when said locking means is actuated, thereby sealing said sleeve against said tube throughout said sleeve length and sealing needle holes in said sleeve, and
            said means for locking being adjustable so as to draw said spaced-apart walls of said casing sections progressively together thereby increasing the radial compression of said casing sections on said sleeve.

2. The injection site guard of claim 1 wherein said casing is generally cylindrical and said two casing sections are generally semicylindrical.

3. The injection site guard of claim 1 wherein said locking means comprises:
    an ear on each said casing section,
        each said ear extending outward from its respective said casing section and located on the longitudinal side of said casing section opposite to the longitudinal side having said hinge, and each said ear being adapted to receive pressure to be brought closer to said other ear to close said casing sections about said sleeve and radially compress said sleeve.

4. The injection site guard of claim 3 wherein said locking means further comprises:
at least one ratchet on one said ear extending toward the other said ear and a corresponding pawl on said other ear extending to meet said ratchet, said ratchet and pawl engaging to lock said casing sections together so that said casing encloses and radially compresses said sleeve, said ratchet and pawl being arranged to allow said casing to be tightened about said sleeve but not loosened.

5. The injection site guard of claim 3 wherein said casing further comprises:
a cylindrical extension from each longitudinal end of said casing, each said extension adapted to enclose said tube where it protrudes from said casing, in order to support said tube for reducing bending stresses imposed on said tube and preventing said stresses from being communicated to the section of said tube enclosed within said sleeve and casing.

6. The injection site guard of claim 5 wherein said casing is a single integral plastic piece incorporating said casing sections, said hinge, said locking means, and said cylindrical extensions.

7. The injection site guard of claim 6 wherein said hinge comprises a longitudinal section of said integral casing of reduced thickness joining said casing sections.

8. The injection site guard of claim 4 wherein there are two ratchets and two corresponding pawls, said ratchets being spaced apart longitudinally along one said ear and said pawls being correspondingly spaced apart longitudinally along said other ear.

* * * * *